United States Patent [19]
MacConnell

[11] Patent Number: 5,209,831
[45] Date of Patent: May 11, 1993

[54] BUFFERLESS ELECTROPHORESIS SYSTEM AND METHOD

[76] Inventor: William P. MacConnell, 1849 Rubenstein Dr., Cardiff, Calif. 92007

[21] Appl. No.: 715,392

[22] Filed: Jun. 14, 1991

[51] Int. Cl.$^5$ .................... B01D 61/42; C25D 13/00; C25B 1/00
[52] U.S. Cl. ............................ 204/299 R; 204/180.1; 204/182.8
[58] Field of Search .................................. 204/299 R

[56] References Cited
U.S. PATENT DOCUMENTS

| | | | |
|---|---|---|---|
| 3,715,295 | 2/1973 | Tocci | 204/180 G |
| 3,865,712 | 2/1975 | Davies | 204/299 R |
| 3,888,759 | 6/1975 | Elson et al. | 204/299 R |
| 4,443,319 | 4/1984 | Chait et al. | 204/299 R |
| 4,608,146 | 8/1986 | Penaluna | 204/299 |

Primary Examiner—John Niebling
Assistant Examiner—Caroline Koestner
Attorney, Agent, or Firm—Baker, Maxham, Jester & Meador

[57] ABSTRACT

A bufferless electrophoresis system for separation of DNA or the like includes a disposable cassette comprising a housing having open ends, a three dimensional gel body in the housing for defining a path, a sample well in a top surface of the gel for introducing a sample into the path at one end thereof, an electrically conductive film closing the ends of the housing and contacting the ends of the gel, and an electrical circuit for selectively applying an electrical potential via the electrically conductive film to the ends of the gel. A holder having spaced apart opposed terminals may be used to hold the cassette and apply the electrical circuit to the cassette.

20 Claims, 1 Drawing Sheet

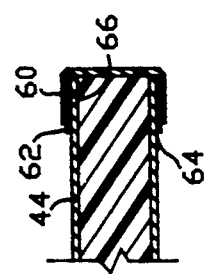
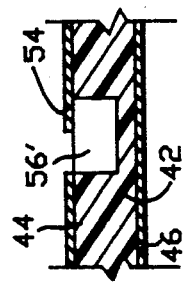
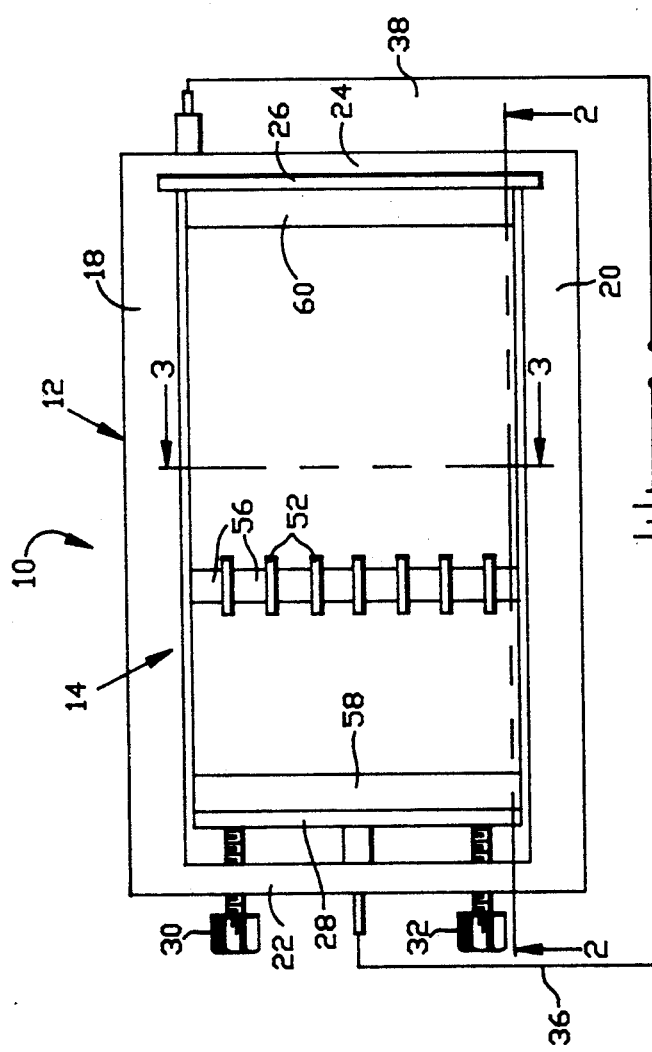
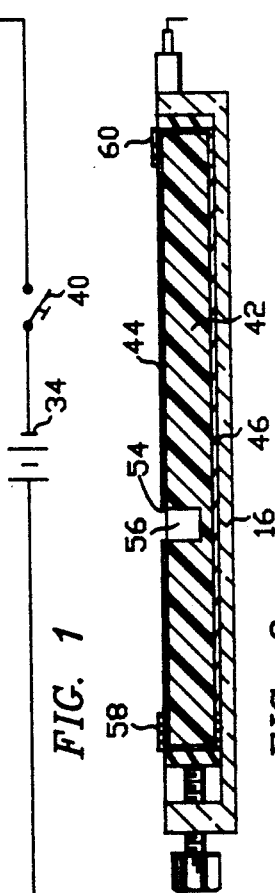
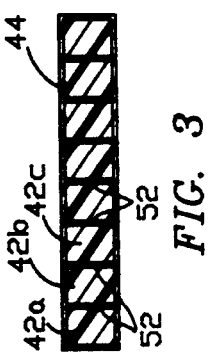

BUFFERLESS ELECTROPHORESIS SYSTEM AND METHOD

BACKGROUND OF THE INVENTION

The present invention relates to the electrophoresis separation of mixtures of molecular particles, such as nucleic acids or proteins and pertains particularly to an improved bufferless method and apparatus for the electrophoresis separation of nucleic acids, proteins and the like.

A great deal of laboratory research is carried out wherein separation of DNA, RNA or protein is widely utilized. This process is widely used in research laboratories for analysis or separation of restriction digest fragments of DNA, where polymerase chain reaction DNA products are analyzed or prepared, where synthetic oligo nucleotides are analyzed or prepared, where protein are analyzed and/or blotted, or any application involving small scale separation of nucleic acid. Electrophoresis separation is typically carried out in a separation medium, such as a gel of agarose or acrylamide. These gels are typically cast in molds consisting of two glass plates to form a slab or in glass tubes to form a cylinder.

Molecular weight or size separation is typically achieved by means of a gel composition formed to create a network of pour sizes which provides a seiving action to separate the molecules. In order to effect the electrophoretic separation, means for connecting an electric field to the separating gel is needed. This is usually accomplished by immersing the ends of the gel slab or cylinder in reservoirs of electrically conductive buffer. These buffers are connected by platinum or carbon electrodes immersed in the fluid to the positive and negative terminals of a power supply, which establishes a voltage gradient of from twenty to three-thousand volts across the separating gel to draw the molecules in the mixture through the gel matrix. This method of attaching the gel to the power supply requires large volumes of buffer to fill reservoirs, immersion of the gel in the buffer or connection via wicks and bulky apparatus for electrophoresis.

One of the major drawbacks of electrophoresis has been the use of these buffers and the complicated equipment required for them. The buffers must be carefully prepared and handled. The buffers are also subject to evaporation with resultant loss of effectiveness due to Ph changes.

Various attempts have been made in the past to overcome the problems inherent in the use of liquid buffer solutions. One such approach is shown for example in U.S. Pat. No. 3,715,295, issued Feb. 6, 1973 to Tocci. This patent describes a device in which wells are formed on each end of the gel, and a semi-solid buffer is placed in the wells over electrodes disposed in the wells. This arrangement, however, still requires large and complicated equipment.

Another attempt to solve this problem is disclosed in U.S. Pat. No. 3,865,712, issued Feb. 11, 1975, which discloses the use of a filter paper as a wick saturated with a buffer placed over the gel. Electrodes are positioned on the filter paper, with electrodes pressed into contact with the filter paper. One problem with this approach is that the wick materials become dried out, with a resultant loss of electrical continuity.

Other attempts to eliminate the use of buffers have included apparatus having its electrodes embedded within the gel. Such known apparatus may be operated at very low voltages, and the current densities must also be kept very low, with the result that the reaction time takes considerable time. Otherwise, the gel surrounding the electrodes would melt and consequently the supply of current would be interrupted since heat cannot be abducted.

U.S. Pat. No. 4,443,319, granted Apr. 17, 1984 to Chait et al discloses a thin film electropheretic device formed with layers with a substrate, electrodes on the substrate and a gel form over both. This approach is suggested for use of very thin open face films oriented in a horizontal plane with very thin films and very low voltage It is therefore desirable that an improved electrophoresis device be available which eliminates the need for buffers and can also be operated at sufficiently high voltages to obtain rapid results.

SUMMARY AND OBJECTS OF THE INVENTION

It is the primary object of the present invention to provide an improved bufferless electrophoresis device capable of reasonable rates of operation.

In accordance with a primary aspect of the present invention, an electrophoresis device comprises a three dimensional body of gel confined in an elongated housing with open ends covered and sealed by an electrically conductive film and provided with sample wells in one surface, and vent ports in the housing at the ends thereof.

BRIEF DESCRIPTION OF THE DRAWING

The above and other objects and advantages of the present invention will become apparent from the following description when read in conjunction with the accompanying drawings wherein:

FIG. 1 is a top plan view of an apparatus in accordance with the invention;

FIG. 2 is a section view taken generally on lines 2—2 of FIG. 1;

FIG. 3 is a section view taken generally on lines 3—3 of FIG. 1;

FIG. 4 is an enlarged detail view showing an end cover and tape sealing the end of the housing; and FIG. 5 is an enlarged detail view, in section, showing an alternate sample well.

DETAILED DESCRIPTION OF PREFERRED EMBODIMENTS

Referring to the drawing, and particularly to FIGS. 1 and 2, there is illustrated an exemplary embodiment of an apparatus in accordance with the invention, designated generally by the numeral 10. The overall apparatus comprises a holder or support housing 12 of a generally box-like open top construction for supporting a cassette, designated generally by the numeral 14. The support housing 12 chiefly functions to support the disposable cassette 14 and to mount terminals to provide means to apply an electrical voltage and/or current to the separation medium within the cassette. In the illustrated embodiment, the holder comprises a generally rectangular box-like open top construction having four upstanding walls, including opposed, side walls and end walls forming a generally rectangular open top cavity within which the cassette is detachably mounted. The holder comprises a bottom panel or wall 16, with upstanding side walls 18 and 20 and opposed end walls 22 and 24. A stationary electrical contact or terminal bar 26 is fixed in one end of the housing at wall 24 and a movable contact or terminal bar 28 is positioned at the other end of the housing, and may be moved such as by means of thumb screws 30 and 32 for biasing it into firm engagement with the ends of the cassette. A source of electrical power, such as a battery 34, is connected by conductors 36 and 38 to the terminal bars 26 and 28. Power to the system may be controlled by means of a conventional switch 40. It is also apparent that the terminal bars can built into the ends of the cassette with leads for direct connection into a source of DC electrical current.

The disposable gel cassette 14 in its preferred form comprises a three dimensional gel body 42 of a suitable gel, such as agarose or acrylamide formed into a three dimensional body between a pair of opposed top and bottom plates 44 and 46 and side plates 48 and 50. In one example, a plurality of partition walls or dividers 52 disposed within the cassette divide the gel body 42 into a plurality of parallel channels or bodies 42a, b, c, etc. In another embodiment, the partition walls are absent and the sample wells separated only by separation medium.

A slot 54 is formed in the top plate 44, and a comb is used in a conventional manner to form sample wells 56 in the gel body 42. The cassette housing is preferably formed of a suitable plastic or the like of a non-conductive material, with at least the top surface 44 being transparent. It may be formed of glass or other suitably well known plastics. A comb 58 is used in a known fashion and inserted in the slot 54 to form wells within the gel slab 42.

Electrical connection of the gel body with the electrical circuit of FIG. 1 is achieved by means of conductive film strips 58 and 60 positioned over the ends of the cassette housing for electrical contact engagement with the ends of the gel body 42 and sealingly closing the ends of the housing. The conductive film may be of the type, such as available under the trademarks "VELOSTAT" or "LAYFLAT" from the 3M Company. This film strip may be attached in any suitable manner by a suitable adhesive bond along the edge of the upper and bottom surfaces of the housing at each end thereof.

I have found a preferred attachment approach, as shown in FIG. 4, which comprises the use of strips of double stick tape 62 and 64 placed along the top and bottom edges of the cassette housing for sealingly bonding the film strip 60 to the end of the housing. The double stick tape is a tape having adhesive on both surfaces thereof, and it is also available from the 3M Company.

Vent ports are provided in the upper surface of the cassette housing along adjacent ends to vent gasses therefrom. These vent ports 66 are covered by the tapes 60 and 62 until just before use of the cassette. The vent ports are then opened by extending the port or hole through the tapes 60 and 62, e.g. by puncturing the tape in line with the holes in the housing. The vent ports may also be pre-formed in the tapes 60, 62 and covered by a peel off strip when ready to use.

The cassette is made by forming or constructing a housing, as above described, and sealing the ends thereof with the tapes 58 and 60. Thereafter, a suitable formulation of gel is poured into the cassette housing, and a comb is inserted into the slot 54 in a known manner to form the wells 56 and to further seal the cassette. The comb is preferably left in place for sealing purposes and is removed and discarded when the cassette is selected for use. Alternatively, the wells may be sealed by means of a peel off tape. This construction enables the cassettes to be prepared in advance, sealed and stored for up to as much as six months under refrigeration prior to use.

Referring to FIG. 5, there is illustrated a alternative construction of the sample wells to obtain greater capacity. In this embodiment, the well 56' is extended beneath the top cover 44 to increase its capacity.

The cassette must have sufficient length to enable complete separation of the DNA or the like without extending into ion depleted areas of the gel near the electrodes. This requires from about three to about six inches. I have found a suitable overall length to be about four and one quarter inches with the sample wells being about two and one half to two and three quarters inches from one end. The width is not critical and can have any desirable number of lanes. The gel should have a thickness of from about 0.05 inches up to about 0.20 inches. The sample wells preferably have a capacity of about 25 microliters.

In operation, when it is desired to run separation sequences for comparison purposes or the like, a cassette as above described is selected and inserted into a holder such as that described above or otherwise connected to a source D.C. current. Suitable samples to be separated are loaded into the respective wells 56 of the cassette. For example, known samples may be run in one lane for comparison to unknown samples in one or more adjacent lanes or channels. After the samples are loaded into the wells, an electrical potential is applied across the cassette by closing switch 40. This results in the DNA, RNA or protein fragments within the samples migrating along the respective lanes. Typically, marker dye is included with the sample. The migration of this marker dye is used to determine the extent of the separation process since the dye runs slightly ahead of most molecules being separated. Monitoring the migration of the marker dye is accomplished by viewing its location relative to the sample wells. This requires that the upper gel be transparent. After a run of from fifteen to sixty minutes, the current is turned off, the cassette removed, and the surface of the gel stained. The various sequences in the parallel lanes can then be compared in a known manner.

While I have illustrated and described my invention by means of specific embodiments, it should be understood that numerous changes and modifications may be made therein without departing from the spirit and scope of the invention as defined in the appended claims. I further assert and sincerely believe that the above specification together with the accompanying drawings contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by me for carrying out the invention.

I claim:

1. A disposable electrophoresis apparatus comprising:
   a housing having opposed top, bottom and side walls defining a three dimensional chamber having opposed open ends;
   a three dimensional body of gel disposed in said chamber and exposed at said open ends;

means in said top wall for introducing a sample into said body of gel;

an electrically conductive thin film disposed in conductive contact with each end of said body of gel and sealingly covering said open ends; and vent means at said ends.

2. A electrophoresis apparatus according to claim 1 wherein said gel is at least 0.05 inches in thickness.

3. A electrophoresis apparatus according to claim 1 wherein said means for introducing a sample comprises a opening through said top wall and a cavity formed in said gel.

4. A electrophoresis apparatus according to claim 1 wherein said vent means comprises a plurality of holes in said top wall at the ends thereof.

5. A electrophoresis apparatus according to claim 4 wherein said vent holes are covered until said unit is ready for use.

6. A electrophoresis apparatus according to claim 1 wherein said housing has a plurality of partition walls defining a plurality of parallel three dimensional chambers having opposed open ends.

7. A electrophoresis apparatus according to claim 1 wherein said housing is at least three inches in length.

8. A electrophoresis apparatus according to claim 7 wherein at least said top wall is transparent.

9. A electrophoresis apparatus according to claim 1 further comprising a holder having opposed spaced apart terminals for conductively engaging said electrically conductive thin film for applying an electrical voltage across the length of said gel.

10. A electrophoresis apparatus according to claim 1 wherein said electrically conductive thin film extends over and is secured to a portion of said top and bottom walls along the end thereof.

11. A electrophoresis apparatus according to claim 10 wherein said electrically conductive thin film is secured to said top and bottom walls by means of double stick tape and sealingly covers said vent means.

12. A portable apparatus for the electrophoresis separation of DNA and the like, said apparatus comprising:

a housing having opposed top, bottom and side walls, and a plurality of partition walls defining a plurality of elongated parallel three dimensional chambers having opposed open ends;

a three dimensional body of gel disposed in each of said chambers and exposed at said open ends;

means including an opening through said top wall and a cavity formed in each of said body of gel for introducing a sample therein;

an electrically conductive thin film disposed in conductive contact with each end of said body of gel and sealingly covering said open ends; and a plurality of vent holes in said top wall at said ends.

13. A electrophoresis apparatus according to claim 12 wherein said gel is at least 0.05 inches in thickness.

14. A electrophoresis apparatus according to claim 13 wherein said electrically conductive thin film extends over and is secured to a portion of said top and bottom walls along the end thereof.

15. A electrophoresis apparatus according to claim 13 wherein said electrically conductive thin film is secured to said top and bottom walls by means of double stick tape and sealingly covers said vent means.

16. A electrophoresis apparatus according to claim 12 further comprising a holder having opposed spaced apart terminals for conductively engaging said electrically conductive thin film for applying an electrical voltage across the length of said gel.

17. A portable apparatus for the electrophoresis separation of DNA and the like, said apparatus comprising:

a generally rectangular box-like housing having opposed top, bottom and side walls, and a plurality of partition walls defining a plurality of elongated parallel three dimensional chambers having opposed open ends;

a three dimensional body of gel at least 0.05 inches in thickness disposed in each of said chambers and exposed at said open ends;

means including an opening through said top wall and a cavity formed in each of said bodies of gel for introducing a sample therein;

an electrically conductive thin film disposed in conductive contact with each end of said body of gel and sealingly covering said open ends; and a plurality of vent holes in said top wall at said ends.

18. A electrophoresis apparatus according to claim 17 wherein said electrically conductive thin film overlaps and is secured to a portion of said top and bottom walls along the end thereof and sealingly covers said vent holes.

19. A electrophoresis apparatus according to claim 17 wherein said said electrically conductive thin film is secured to said top and bottom walls by means of double stick tape.

20. A electrophoresis apparatus according to claim 19 further comprising a generally rectangular open top holder having opposed spaced apart elongated bar terminals for engaging across the ends of said housing and conductively engaging said electrically conductive thin film for applying an electrical voltage across the length of said gel.

* * * * *